(12) United States Patent
Li et al.

(10) Patent No.: US 12,247,062 B2
(45) Date of Patent: Mar. 11, 2025

(54) SOLUBLE UNIVERSAL ADCC-ENHANCING SYNTHETIC FUSION GENE AND PEPTIDE TECHNOLOGY AND ITS USE THEREOF

(71) Applicant: 1GLOBE BIOMEDICAL CO., LTD., Beijing (CN)

(72) Inventors: Chiang J. Li, Cambridge, MA (US); Shyam Unniraman, Newton, MA (US)

(73) Assignee: 1GLOBE BIOMEDICAL CO., LTD., Beijing (CN)

( * ) Notice: Subject to any disclaimer, the term of this patent is extended or adjusted under 35 U.S.C. 154(b) by 852 days.

(21) Appl. No.: 15/532,770

(22) PCT Filed: Dec. 8, 2015

(86) PCT No.: PCT/US2015/064572
§ 371 (c)(1),
(2) Date: Jun. 2, 2017

(87) PCT Pub. No.: WO2016/094456
PCT Pub. Date: Jun. 16, 2016

(65) Prior Publication Data
US 2017/0362299 A1  Dec. 21, 2017

Related U.S. Application Data

(60) Provisional application No. 62/200,557, filed on Aug. 3, 2015, provisional application No. 62/089,097, filed on Dec. 8, 2014.

(51) Int. Cl.
*C07K 14/735* (2006.01)
*C07K 16/28* (2006.01)
*C07K 16/46* (2006.01)
*A61K 38/00* (2006.01)
*A61K 39/00* (2006.01)

(52) U.S. Cl.
CPC .... *C07K 14/70535* (2013.01); *C07K 16/2806* (2013.01); *C07K 16/2809* (2013.01); *C07K 16/46* (2013.01); *A61K 38/00* (2013.01); *A61K 2039/505* (2013.01); *C07K 2317/24* (2013.01); *C07K 2317/622* (2013.01); *C07K 2317/732* (2013.01); *C07K 2317/92* (2013.01); *C07K 2319/00* (2013.01); *C07K 2319/74* (2013.01)

(58) Field of Classification Search
CPC ............................. C07K 19/00; C07K 16/468
See application file for complete search history.

(56) References Cited

U.S. PATENT DOCUMENTS

| | | | | | |
|---|---|---|---|---|---|
| 6,048,526 | A * | 4/2000 | Skibbens | ........... | C07K 16/2809 424/144.1 |
| 7,271,149 | B2 * | 9/2007 | Glaesner | ................. | C07H 21/04 514/7.2 |
| 2004/0213791 | A1 * | 10/2004 | Bander | .............. | A61K 51/1072 424/155.1 |
| 2007/0059806 | A1 * | 3/2007 | Arnon | .................. | C12N 15/115 435/91.1 |
| 2007/0292416 | A1 | 12/2007 | Rother | | |
| 2008/0213256 | A1 * | 9/2008 | Kufer | ...................... | A61P 31/12 424/133.1 |
| 2008/0219978 | A1 * | 9/2008 | Ellsworth | ............... | A61P 25/00 424/134.1 |
| 2008/0292646 | A1 * | 11/2008 | Benhar | .................. | C07K 14/21 424/178.1 |
| 2012/0294857 | A1 | 11/2012 | Sentman | | |
| 2013/0281677 | A1 | 10/2013 | Wilson | | |
| 2015/0037334 | A1 * | 2/2015 | Kufer | ................. | C07K 16/2809 424/134.1 |

FOREIGN PATENT DOCUMENTS

| | | | |
|---|---|---|---|
| AU | 2015360642 B2 | | 6/2016 |
| WO | WO2005/040220 | * | 5/2005 |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Lobo (J. Immunol., vol. 180, p. 1769-1779, 2008) (Year: 2008).*
Mota (Scandinavian Journal of Immunology, vol. 59, p. 278-284, 2004) (Year: 2004).*
Cho-Chung (Biochimica et Biophysica Acta, vol. 1762, p. 587-591, 2006) (Year: 2006).*
Harrison (Protein Engineering, vol. 11, No. 3, p. 225-232, 1998) (Year: 1998).*
Mancardi (Blood, vol. 121, No. 9, p. 1563-1573, 2013) (Year: 2013).*
Hamann et al., "Gemtuzumab ozogamicin, a potent and selective anti-CD33 antibody-calicheamicin conjugate for treatment of acute myeloid leukemia," Bioconjugate Chem. Jan.-Feb. 2002, vol. 13, No. 1, 47-58.
Biglari A. et al., "Human monocytes expressing a CEA-specific chimeric CD64 receptor specifically target CEA-expressing tumour cells in vitro and in vivo," Gene Therapy, Apr. 8, 2006, vol. 13: 602-610.
Moore G. L. et al., "A novel bispecific antibody format enables simultaneous bivalent and monovalent co-engagement of distinct target antigens," mAbs, Nov. 1, 2011, vol. 3, No. 6, pp. 546-557.
Malygin A. M. et al., "Promotion of natural killer cell growth in vitro by bispecific (anti-CD3 x anti-CD16) antibodies," Immunology., Jan. 8, 1994, vol. 81, No. 1, pp. 92-95.

(Continued)

Primary Examiner — Michael Allen
(74) Attorney, Agent, or Firm — Milstein Zhang & Wu LLC; Duan Wu, Esq.

(57) ABSTRACT

Novel synthetic biology-based ADCC technologies are provided that enhance or enable ADCC responses, for example, through a rationally-designed soluble universal ADCC enhancer protein (SUAEP) where a high-affinity CD3-binding domain is fused to a high-affinity Fc-binding domain. The SUAEP technology can be used to prevent or treat cancers, infectious, inflammatory or autoimmune diseases, and other diseases where elimination of diseased cells is desirable.

6 Claims, 18 Drawing Sheets
Specification includes a Sequence Listing.

(56) References Cited

OTHER PUBLICATIONS

First Examination Report in corresponding New Zealand Application Serial No. 732073, mailed Apr. 6, 2018.
Extended European search report in corresponding European Patent Application No. 15867381.4, mailed Apr. 26, 2018.
Search report and written opinion in corresponding Singapore Application Serial No. 8212432, mailed Jun. 20, 2018.
Examination Report No. 1, in corresponding Australian Application Serial No. 2015360642, Emailed Jun. 29, 2018.
Hu et al. "Treatment with CD20-specific antibody prevents and reverses autoimmune diabetes in mice," J Clin Invest. 2007, 117(12): 3857-67.
Xiu et al. "B Lymphocyte Depletion by CD20 Monoclonal Antibody Prevents Diabetes in Nonobese Diabetic Mice despite Isotype-Specific Differences in FcγR Effector Function," J Immunol. 2008, 180(5):2863-75.
Barr et al. "B cell depletion therapy ameliorates autoimmune disease through ablation of IL-6-producing B cells," J Exp Med. 2012, 209(5): 1001-10).
Yanaba et al. "B Cell Depletion Delays Collagen-Induced Arthritis in Mice: Arthritis Induction Requires Synergy between Humoral and Cell-Mediated Immunity," J Immunol. 2007, 179(2): 1369-80.
Klein et al. "HIV therapy by a combination of broadly neutralizing antibodies in humanized mice," Nature, 2012, 492(7427): 118-22.
Jaworski et al. "Neutralizing Polyclonal IgG Present during Acute Infection Prevents Rapid Disease Onset in Simian-Human Immunodeficiency Virus SHIV(SF162P3)-Infected Infant Rhesus Macaques," J Virol. 2013, 87(19): 10447-59.

Wilson et al., "HIV-1-Specific CTL Responses Primed In Vitro by Blood-Derived Dendritic Cells and Th1-Biasing Cytokines," J Immunol., 1999, 162:3070-78.
International Preliminary Report of Patentability for PCT/US2015/064572, issued Jun. 13, 2017.
Takia, T., "Roles of Fc Receptors in Autoimmunity," Nat Rev Immunol. 2:580-592 (2002).
Nimmerjahn, F. and Ravetch, J.V., "Fcgamma receptors as regulators of immune responses," Nat Rev Immunol. 8:34-47, (2008).
Galon, et al. "Affinity of the interaction between Fc gamma receptor type III (FcγRIII) and monomeric human IgG subclasses. Role of FcγRIII glycosylation," Eur J Immunol. 27: 1928-1932, (1997).
EPO Communication in corresponding European Patent Application No. 15867381.4, mailed Mar. 7, 2019.
EPO Communication in corresponding European Patent Application No. 15867381.4, mailed Sep. 24, 2019.
EPO Communication in corresponding European Patent Application No. 15867381.4, mailed Jan. 21, 2020.
EPO Decision to Grant in corresponding European Patent Application No. 15867381.4, mailed Jan. 7, 2022.
Notice of Acceptance in corresponding Australian Application Serial No. 2015360642, mailed Mar. 20, 2019.
Notice of Allowance in corresponding Canadian Patent Serial No. 2968987, mailed Dec. 23, 2021.
Notice of Acceptance in corresponding Singapore Application Serial No. 11201704124Y, mailed Aug. 17, 2021.
Notice of Acceptance in corresponding New Zealand Application Serial No. 732073, mailed Apr. 8, 2019.

* cited by examiner

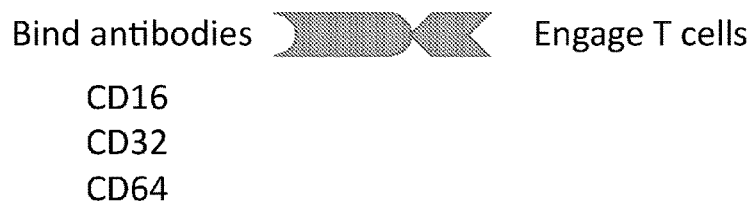
Bind antibodies　　　　Engage T cells
CD16
CD32　　　　　　　　　　　　　　Figure 1
CD64
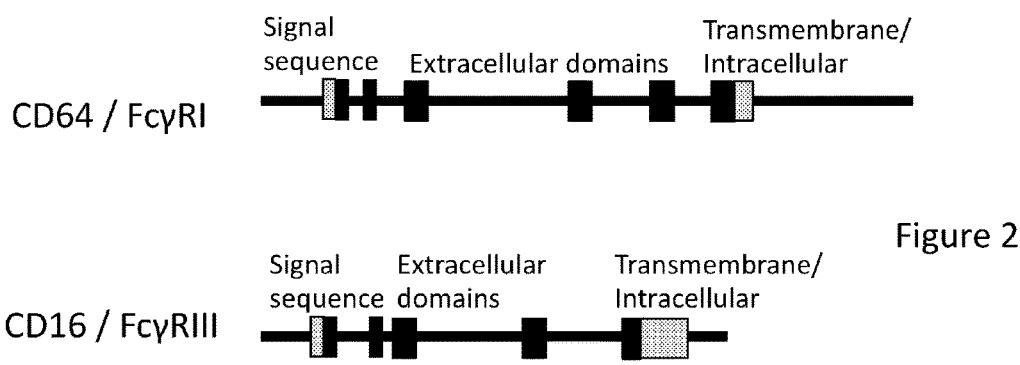
Figure 2

CD64 ectodomain (Exon-based) (SEQ ID NO:1)
1-281
MWFLTTLLLWVPVDGQVDTTKAVITLQPPWVSVFQEETVTLHCEVLHLPGSSSTQWFLNGTATQT
STPSYRITSASVNDSGEYRCQRGLSGRSDPIQLEIHRGWLLLQVSSRVFTEGEPLALRCHAWKDK
LVYNVLYYRNGKAFKFFHWNSNLTILKTNISHNGTYHCSGMGKHRYTSAGISVTVKELFPAPVLN
ASVTSPLLEGNLVTLSCETKLLLQRPGLQLYFSFYMGSKTLRGRNTSSEYQILTARREDSGLYWC
EAATEDGNVLKRSPELELQVL

Figure 3

Spacer+hOKT3 (SEQ ID NO:2)
SSGGGGSQVQLVQSGGGVVQPGRSLRLSCKSSGYTFTRYTMHWVRQAPGKGLEWIGYINPSRGY
TNYNQKVKDRFTISRDNSKNTAFLQMDSLRPEDTGVYFCARYYDDHYCLDYWGQGTPVTVSSVE
GGSGGSGGSGGSGGVDDIQMTQSPSSLSASVGDRVTITCRASSSVSYMNWYQQTPGKAPKRWIY
DTSKVASGVPSRFSGSGSGTDYTFTISSLQPEDIATYYCQQWSSNPLTFGQGTKLQIT

Figure 4

Fusion protein (SEQ ID NO:3)

MWFLTTLLLWVPVDGQVDTTKAVITLQPPWVSVFQEETVTLHCEVLHLPGSSSTQWFLNGTATQTSTPS
YRITSASVNDSGEYRCQRGLSGRSDPIQLEIHRGWLLLQVSSRVFTEGEPLALRCHAWKDKLVYNVLYY
RNGKAFKFFHWNSNLTILKTNISHNGTYHCSGMGKHRYTSAGISVTVKELFPAPVLNASVTSPLLEGNL
VTLSCETKLLLQRPGLQLYFSFYMGSKTLRGRNTSSEYQILTARREDSGLYWCEAATEDGNVLKRSPEL
ELQVLSSGGGGSQVQLVQSGGGVVQPGRSLRLSCKSSGYTFTRYTMHWVRQAPGKGLEWIGYINPSRGY
TNYNQKVKDRFTISRDNSKNTAFLQMDSLRPEDTGVYFCARYYDDHYCLDYWGQGTPVTVSSVEGGSGG
SGGSGGSGGVDDIQMTQSPSSLSASVGDRVTITCRASSSVSYMNWYQQTPGKAPKRWIYDTSKVASGVP
SRFSGSGSGTDYTFTISSLQPEDIATYYCQQWSSNPLTFGQGTKLQIT

Figure 5

Fusion gene (SEQ ID NO:4)
ATGTGGTTTCTGACTACACTGCTGCTGTGGGTGCCCGTGGATGGACAGGTGGATACTACAAAAGC
CGTGATTACACTGCAGCCCCCTTGGGTGTCTGTCTTCCAGGAGGAAACCGTGACACTGCACTGCG
AGGTCCTGCATCTGCCAGGCAGCTCCTCTACCCAGTGGTTTCTGAACGGAACTGCTACCCAGACA
TCTACTCCCAGTTACCGCATCACAAGCGCATCCGTGAATGACAGCGGCGAGTATCGATGCCAGCG
GGGGCTGTCAGGTCGAAGCGATCCAATCCAGCTGGAAATTCACCGGGGGTGGCTGCTGCTGCAGG
TGAGTTCAAGGGTCTTCACCGAGGGTGAACCCCTGGCACTGAGGTGTCACGCCTGGAAGGACAAA
CTGGTGTACAACGTCCTGTACTATAGAAATGGCAAGGCCTTCAAGTTCTTTCATTGGAACAGCAA
TCTGACTATCCTGAAGACCAACATTTCTCACAATGGAACCTACCATTGCAGCGGAATGGGGAAGC
ATCGCTATACTTCTGCTGGGATCAGTGTGACCGTCAAAGAACTGTTCCCAGCTCCCGTGCTGAAC
GCATCCGTCACATCTCCTCTGCTGGAGGGGAATCTGGTGACACTGTCCTGTGAAACTAAGCTGCT
GCTGCAGCGGCCAGGACTGCAGCTGTACTTCTCCTTTTATATGGGCTCTAAAACCCTGAGAGGAC
GCAACACAAGCTCCGAGTACCAGATTCTGACTGCCCGGAGGGAAGACAGCGGGCTGTATTGGTGC
GAGGCCGCTACCGAAGATGGTAATGTGCTGAAGAGGTCCCCCGAGCTGGAACTGCAGGTGCTGTC
TAGTGGCGGAGGGGGTAGTCAGGTGCAGCTGGTCCAGTCCGGAGGAGGAGTGGTCCAGCCTGGCA
GGTCACTGAGACTGAGCTGTAAGTCAAGCGGATACACCTTCACAAGATATACTATGCACTGGGTG
CGCCAGGCTCCTGGTAAAGGACTGGAGTGGATCGGGTACATTAACCCTAGCAGAGGTTACACAAA
CTATAATCAGAAGGTGAAAGACCGCTTCACAATCTCCCGAGATAACTCTAAAAATACTGCCTTTC
TGCAGATGGACTCCCTGAGACCTGAGGATACCGGCGTGTACTTTTGCGCTCGCTACTATGACGAT
CATTACTGTCTGGATTATTGGGGACAGGGGACCCCAGTGACAGTCTCCTCTGTGGAAGGTGGCAG
TGGAGGGTCAGGTGGCAGCGGAGGGTCCGGTGGAGTGGACGATATCCAGATGACCCAGTCTCCCA
GTTCACTGTCTGCCAGTGTGGGCGACCGGGTCACTATTACCTGCAGGGCTAGCTCCTCTGTGAGC
TACATGAATTGGTATCAGCAGACCCCTGGCAAGGCACCAAAACGATGGATCTACGATACCAGTAA
GGTGGCCTCAGGAGTCCCAAGCCGGTTCTCAGGTAGCGGCTCCGGAACAGACTATACCTTCACCA
TCAGTTCACTGCAGCCTGAGGATATTGCCACTTACTATTGTCAGCAGTGGAGTAGTAATCCTCTG
ACATTCGGACAGGGAACCAAACTGCAGATCACATAA

Figure 6

SAMPLE LOAD

PURIFIED PROTEIN

SOLUBLE UNIVERSAL ADCC-ENHANCING SYNTHETIC FUSION GENE AND PEPTIDE TECHNOLOGY AND ITS USE THEREOF

CROSS-REFERENCE TO RELATED APPLICATIONS

This application is a national phase application under 35 U.S.C. 371 of the international application PCT/US2015/064572, filed Dec. 8, 2015 which, in turn, claims priority to and the benefit of U.S. provisional patent application Serial Nos. 62/089,097, filed on Dec. 8, 2014, and 62/200,557, filed on Aug. 3, 2015, both of which are incorporated herein by reference in their entirety.

TECHNICAL FIELD

The invention relates to synthetic biology products and processes that can be used to enable immune effector cells, particularly, T cells, to mediate antibody-dependent cellular cytotoxicity (ADCC) as well as methods of using them in the treatment and prevention of cancer, infectious diseases, inflammatory and autoimmune diseases and other diseases.

Sequence listings and related materials in the ASCII text file named "GHI003US1-SEQ_ST25.txt" and created on Aug. 22, 2019 with a size of about 12 kilobytes, is hereby incorporated by reference.

BACKGROUND OF INVENTION

Mammals, especially higher vertebrates including human, have developed highly complex immune systems that use multiple mechanisms and effectors to detect, destroy, or at least contain foreign pathogens as well as diseased or stressed autologous cells. These diseased cells may have been infected by virus or bacteria, or have become cancerous.

One of the mechanisms for the immune system to recognize and eliminate diseased host cells and invading intracellular microorganisms (e.g., viruses, bacteria or parasites) is through cell-mediated cytotoxicity, which can be carried out by a number of leukocytes and proteins. These potentially cytotoxic effectors include: from the lymphoid lineage—Natural Killer (NK) cells and cytotoxic T lymphocytes (CTLs); and from the myeloid lineage—macrophages, neutrophils and eosinophils.

An important way for the immune system to unleash cell-mediated cytotoxicity relies on antibodies. Over the past decade, monoclonal antibodies (mAbs) that target tumor-specific cell-surface proteins have become a popular therapeutic approach against cancers. Several mAbs have entered routine clinical practice including rituximab (RITUXAN, MABTHERA), trastuzumab (HERCEPTIN) and cetuximab (ERBITUX). The popularity of mAbs is a result of their bifunctional nature. One end of an antibody (Fab) can be made exquisitely specific to a particular tumor protein without altering the other end (Fc) which recruits a variety of effector cells and proteins that kill the tumor cell.

Specifically, after recognizing and binding antigens on the surface of a target cell first, antibodies act as an adapter and proceed to activate the cytotoxic capability of immune effector cells through a second binding with certain receptors on those effector cells. This is called the antibody-dependent cellular cytotoxicity (ADCC). For example, in the context of innate immunity against cancer, ADCC is primarily mediated by natural killer (NK) cells (and, to a lesser extent, neutrophils, monocytes and macrophages) that express a relatively low-affinity Fc receptor (FcγRIIIa, also known as CD16a) that is only activated upon its binding with the Fc fragments of antibodies coating a multivalent antigen on a target diseased cell (e.g., a tumor cell). This binding triggers the release of cytotoxic granules like perforin and granzyme (as well as many cytokines including IFN-7), leading to the lysis of the target cell. The importance of ADCC has been shown both in vitro as well as in animal studies. Moreover, several clinical studies have shown that patients carrying a lower affinity variant of CD16 (F158) have worse clinical outcomes.

However, ADCC efficacy, as primarily mediated by endogenous natural killer (NK) cells, is limited in the body due to a number of physiological as well as pathological reasons as explained below (to the extent that endogenous Cytotoxic T lymphocytes participate in tumor clearance at all, their efficacy have also been found to be very limited and lacking).

First, most cells involved in ADCC such as macrophages and neutrophils do not tend to proliferate when they are activated. NK cells also have limited proliferation potential in response to activation, and they also rapidly die off. Therefore, natural ADCC response in the body risks being overwhelmed by disease progression (e.g., viral infection, cancer) even if the ADCC effectors recognize antibodies coating diseased cells.

Second, many of the ADCC effector cells also express inhibitory receptors that dampen their immune responsiveness, thereby instituting a system of balances and checks. These receptors include inhibitory KIRs (killer immunoglobulin-like receptors) for $CD56^{low}$ NK cells, FcγRIIb on monocytes and B cells, and CTLA-4 (CD152) and PD-1 (Programmed-Death-1, CD279) for T cells. Cancer cells and viruses counteract body's ADCC-based defense system by abnormally amplifying such inhibitory pathways.

Third, the main Fc receptor on ADCC effector cells, FcγRIIIa (CD16a), has a relatively low affinity ($Kd \approx 10^{-6}$ M) for antibodies—even the V158 variant of the receptor has only a two-fold higher affinity compared to the ineffective F158 form of the receptor. This is one mechanism through which cancer cells become resistant to some therapeutic monoclonal antibodies (mAbs) once the density of the cell surface targets fall below a certain level.

In view of its natural limitations in proliferation and affinity as well as further depression through inhibitory Fc receptors in the setting of a disease, such as cancer or other diseases, the body's ADCC function has great potential that is never fully realized. Therefore, synthetic biology represents a novel and highly desirable approach to unleash the full potential of ADCC activity in the prevention and treatment of human diseases.

BRIEF SUMMARY OF THE INVENTION

The present invention ushers in new approaches to improve the immune system's defense against cancer, infections and other diseases. The present invention devises a novel, free-associating, Adapter-like ADCC Enhancer that couples the cytotoxicity and proliferative potential of T cells to antibody-based therapy.

According to the present invention, a fusion protein is provided as a free-associating and circulating adapter that brings an antibody targeting a diseased cell (e.g., a tumor cell) into contact with $CD3^+$ T cells. This new adapter molecule is soluble and can be injected into the blood of the patient to access most tissue compartments. This Adapter-like ADCC Enhancer has two components as follows: (a) a high-affinity Fc-binding domain; and (b) a high-affinity CD3-binding domain. The rationale for this approach is: this Adapter-like ADCC Enhancer will bind to a tumor cell already coated with one or more therapeutic antibodies, and the Enhancer can also bind to $CD3^+$ T cells. Once in close proximity or in contact with a T cell, the antibodies that coat the tumor cell will cause crosslinking of the CD3s on the surface of T cell and lead to activation of the T cell and, eventually, lysis of the tumor cell.

The ADCC Enhancer of the present invention can be used either in combination with an antibody therapy or by itself to target diseased cells recognized or bound by a naturally occurring antibody.

In a first aspect, the present invention sets out to build high-affinity Fc receptors or antibody fragments, such as those with higher affinity for a natural antibody than wild-type human CD16 (e.g., the most common form of human CD16, i.e., the common F158 variant). The Receptor (hereinafter used as a term to encompass embodiments resembling more traditional cell-surface receptor and embodiments based on antibody fragment(s)), in part or in whole, may be borrowed from another macromolecule in the immune system or engineered anew. Having a high-affinity Fc Receptor enables efficient binding with the shared Fc fragment of antibodies that target a wide variety of cell surface antigens and thereby a wide variety of diseases and indications. This is a great advantage compared to antigen-dependent immunotherapy where a different antibody needs to be built against each specific antigen.

In another aspect, focusing on building the soluble, Adapter-like ADCC Enhancer, a high-affinity CD3-binding domain is fused to the high-affinity Fc-binding domain or Receptor described in the first aspect. Examples of such high-affinity CD3-binding domains include OKT3 and novel anti-CD3 scFv. The high-affinity Fc-binding domain, in various embodiments, may be selected from the group consisting of the ectodomain of CD64, a high-affinity CD16 variant, and an antibody fragment with high-affinity for human Fc.

In another aspect, the invention provides a pharmaceutical composition that includes the fusion protein of the invention which, in turn, comprises a high-affinity Fc-binding domain, and a high-affinity CD3-binding domain. The pharmaceutical composition further includes a pharmaceutically acceptable excipient.

In a related aspect, the invention provides a method of treating a subject in need thereof for a condition therapeutically, said method comprising administering to said subject a therapeutically effective amount of the pharmaceutical composition of the invention. The method may further include a step of administering a therapeutic antibody against at least one cell-surface antigen indicative of said condition. In one embodiment, the antibody comprises an Fc region substantially similar to the human IgG4. The condition being treated may be a cancer, an inflammatory disease, an autoimmune disease, transplant rejection and an infection, and so on.

In yet another aspect, the invention provides a method of treating a subject in need thereof for similar conditions prophylactically, said method comprising administering to said subject a prophylactically effective amount of the pharmaceutical composition of the invention. The method may further include a step of administering a vaccine against said condition. In one embodiment, the condition is a cancer.

BRIEF DESCRIPTION OF FIGURES

FIG. 1 schematically depicts an Adapter-like ADCC Enhancer according to the present invention.

FIG. 2 schematically depicts the exons of CD64 and CD16. CD64 has an additional immunoglobulin fold, and hence, exon, in the extracellular region. This additional fold is credited for CD64's higher Fc-affinity.

FIG. 3 lists the amino acid sequence (SEQ ID NO:1) for the Fc-binding domain of the Adapter-like ADCC Enhancer according to an embodiment of the present invention. Specifically, the domain in this embodiment includes the ectodomain of CD64 based on exon boundaries.

FIG. 4 lists the amino acid sequence (SEQ ID NO:2) for the anti-CD3 domain of the Adapter-like ADCC Enhancer according to an embodiment of the present invention. Specifically, the domain in this embodiment includes two spacer/linker sequences (underlined) and a humanized version of OKT3 sequence.

FIG. 5 lists the amino acid sequence (SEQ ID NO:3) for the entire Adapter-like ADCC Enhancer according to the embodiment represented in FIGS. 3 and 4.

FIG. 6 lists a DNA sequence (SEQ ID NO.4) for the entire Adapter-like ADCC Enhancer according to the embodiment represented in FIG. 5.

DETAILED DESCRIPTION OF INVENTION

I. Definition

Figure 7:
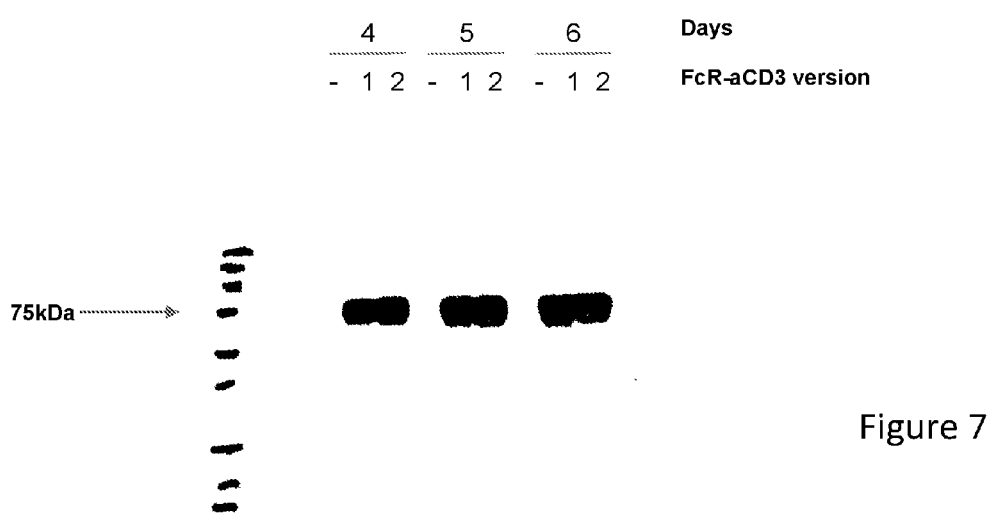
FIG. 7 is a photographic image of an immunoblot (western blot) showing time course of overexpression of two versions of the soluble, Adapter-like ADCC Enhancer in Expi293 cells. Both versions had the same CD64-OKT3 fusion protein sequence and only differ in their respective nucleotide sequences (Lanes 1 and 2). The protein was secreted into the media. Predicted molecular weight was 58 kDa; the anti-CD64 antibody picked a band at 75 kDa probably due to glycosylation.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341), and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The term "antibody" or "Ab", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art, and include but are not limited to a single-chain Fv(scFv), Fab, F(ab'), F(ab')$_2$, a single domain, and the like. Non-limiting embodiments of which are discussed below.

CD16 is expressed as two distinct forms, CD16a and CD16b, which are products of two different yet highly homologous genes. CD16a is a polypeptide-anchored transmembrane protein while CD16b is a glycosylphosphatidylinositol-anchored protein. As used herein, CD16 refers to both forms of the protein, unless inappropriate as would be apparent to one skilled artisan.

Effector cells useful in practicing the present invention may be autologous, syngeneic or allogeneic, with the selection dependent upon the disease to be treated and means available.

II. Compositions

The present invention discloses the Soluble Universal ADCC Enhancer Protein (SUAEP) technology, which provides off-the-shelf, adapter-like, soluble universal ADCC enhancing proteins that can be applied, in theory, universally to enhance therapeutic efficacy of antibodies. The enhancing mechanisms can include at least the following aspects:

1. ADCC is important for the efficacy of antibody therapies (e.g., RITUXAN® (rituximab) or HERCEPTIN® (trastuzumab) treatment). Several studies have shown that the patients homozygous for the low affinity variant of CD16 (158F) have poorer prognosis.
2. Even for patients with the relatively high affinity variant of CD16, ADCC may be suppressed as discussed earlier for a variety of reasons, e.g., an immunosuppressive environment, engagement of inhibitory receptors or inability of effector cells to proliferate.
3. Complement system is also important for RITUXAN® (Rituximab) efficacy. For instance, although CLLs is an indolent B cell cancer, patients are often refractory to RITUXAN® (rituximab) because they are either deficient in complement or because complement gets depleted soon after the start of a RITUXAN® (rituximab) treatment (Xu et al., 2011, International Journal of Cancer 128: 2193-2201; Kennedy et al., 2004, Journal of Immunology 172 (5) 3280-3288).

In all these cases, the addition of the ADCC Enhancer will be able to circumvent the problem and recruit cytotoxic T cells to the cancer cells.

In addition, the SUAEP technology as provided by the present invention will be useful in reducing the amounts of antibodies that need to be used for therapy and thereby minimize (a) the non-specific side effects of the antibody; and (b) reduce the chance of developing an anti-antibody response. It should be noted that even a fully human antibody has unique CDR3s that can trigger an immune response. Reducing the amount of antibody used in therapy will reduce the chance of triggering this response.

Adapter for T Cells

According to the an embodiment of the present invention, a fusion protein that functions as a circulating, free-associating Adapter-like ADCC Enhancer has two components: a high-affinity Fc-binding domain that couples to antibodies, and a high-affinity CD3-binding domain that engages T cells (FIG. 3).

(a) Fc-Binding Domain

The Fc-binding domain for the Adapter-like ADCC Enhancer can come from multiple sources, including:

(i) Ectodomain of CD64 (FcγR1):

FcγR1 is the high affinity Fc receptor (Kd≈$10^{-9}$ M for IgG1 and IgG3) present on macrophages and neutrophils and is responsible for antibody-mediated phagocytosis and mediator release. FcγRI includes a glycoprotein a chain whose extracellular domain is comprised of three immunoglobulin domains that are responsible for binding to antibodies.

According to an embodiment of the invention, parts or all of the ectodomain of CD64 (FcγRI) is fused to a suitable CD3-binding domain to generate an Adapter-like Enhancer that mediates ADCC. Advantageously, with the ectodomain being native to the body, the Enhancer in this embodiment is syngeneic and, therefore, non-immunogenic.

(ii) High-Affinity Variant of CD16:

In another embodiment of the invention, the Fc-binding domain of the Adapter-like ADCC Enhancer of the present invention incorporates parts or all of the ectodomain of a CD16 (FcγRIII) variant with improved affinity to the Fc fragment of antibodies. In an embodiment, the sequence for the Fc-binding domain is generated by random mutagenesis of the binding region of FeyRIIIa and selected by using the most common CD16 variant (F158) as benchmarking control.

(iii) High-Affinity ScFv:

In a further embodiment, the Fc-binding domain of the present invention incorporates an antibody fragment engineered with high-affinity for Fc (preferably human Fc). In an embodiment, the antibody fragment is an ScFv (single-chain variable fragment). In an alternative embodiment, the fragment is a Fab (fragment antigen-binding). The antibody fragment should exhibit higher Fc affinity than a benchmark receptor, e.g., CD16. Methods to engineer such antibody fragments are well known to one skilled in the art, e.g., through the use of hybridomas available commercially. For example, human Fc domain is injected into lab animals (e.g., mice) over a period of time. B cells isolated from the animals' spleen are fused with myeloma cells and screened for clones that produce high-affinity monoclonal antibodies against the Fc domain. These candidate antibodies can be humanized, deimmunized and/or converted in Fab or ScFv versions by standard methods. Alternatively, fully human antibodies can be obtained through screening libraries (e.g. phage display, yeast or mammalian cell-based) for high affinity clones or monoclonal antibodies from animals with humanized immune systems.

(b) CD3-Binding Domain

The CD3-binding domain, preferably with high affinity, can also be made from multiple sources.

For example, this domain can be derived from OKT3, which is an anti-CD3 monoclonal antibody that was the first monoclonal to be approved for human use in 1986. This is a mouse monoclonal antibody and over the years it has been modified multiple times to both humanize it and to make it less immunogenic (deimmunized). In one embodiment, the CD3-binding domain comprises the scFv portion of the OKT3 antibody, preferably, the deimmunized, humanized (dhOKT3) version.

In other embodiments of the present invention, novel anti-CD3 scFv can be made using methods similar to those described in Section (a)(iii) above with regard to high-affinity Fc-binding scFv.

In a preferred embodiment, the Adapter-like ADCC Enhancer is a fusion protein where the CD64 ectodomain is coupled to the dhOKT3 scFv.

It should be noted that this therapeutic can be used to enhance the efficacy of commercially available anti-cancer antibodies. However, this therapeutic can also be used as monotherapy to enhance the efficacy of the body's natural antibodies that are unable to clear tumors because of intrinsic low ADCC activity of a patient.

III. Therapeutics and Vaccines

Clinical implications of the ADCC Enhancers for cancer-treatment can be tested using human cancer cells in conjunction with commercially available therapeutic antibodies. For example, Daudi cells are treated with (1) Rituximab (trade name RITUXAN®), an antibody that targets CD20 implicated in lymphoma, autoimmune diseases and transplant rejection, resulting in effector cell activation, degranulation and proliferation, (2) $CD8^+$ cytotoxic T cells, and (3) the Adapter-like ADCC Enhancer of the present invention. In one embodiment, the ADCC enhancer of the invention is used in combination with the existing therapeutic antibody such as Rituximab. Target cell killing is also observed. In vivo testing is performed using commercially available NOD.scid. $IL2R\gamma^{-/-}$ mice which have very low T and B cells and no NK cells. Alternatively, NOD.Scid mice which have very low T and B cells and reduced NK cells are used. These mice are engrafted with labeled Daudi cells and tumor growth is observed and measured using any suitable imaging technique. In mice receiving Rituximab and immune effector cells transduced with the ADCC Enhancer of the present invention, sustained periods of tumor remission, regression, or long-term non-progression are observed.

In another example, SK-BR-3 or MDA-MB-231 are treated with (1) CD8+ cytotoxic T cells, (2) the Adapter-like ADCC Enhancer of the present invention, and (3) Trastuzumab (trade name HERCEPTIN®) which targets the HER2/neu implicated in breast cancers, resulting in effector cell activation, degranulation and proliferation. Target cell killing is also observed. In vivo anti-tumor potency of the ADCC Enhancer is observed in mice models similar to the example described immediately above.

The clinical use of the ADCC Enhancer of the present invention in autoimmunity can be tested using one of the well-established mouse models for each specific disease. For instance, antibody-mediated B cell deletion has been shown to prevent and even reverse type-1 diabetes in NOD mice. However, this effect is limited by the low affinity of the Fc receptors (Hu et al. J Clin Invest. 2007, 117(12): 3857-67; Xiu et al. J Immunol. 2008, 180(5):2863-75). Control mice are compared with mice receiving either anti-CD19 or anti-CD20 antibodies alone or in combination with the ADCC Enhancer of the present invention. The mice receiving the ADCC Enhancer show delayed onset of disease or sustained reversal of symptoms.

Similar experiments can be performed in other mouse models where antibody-mediated depletion has been shown to impact diseases such as multiple sclerosis, or experimental autoimmune encephalomyelitis (Barr et al. *J Exp Med.* 2012, 209(5): 1001-10)), arthritis (Yanaba et al. *J Immunol.* 2007, 179(2): 1369-80), and so on.

The clinical use of the ADCC Enhancers in viral infections such as HIV infection can be tested using well-established humanized mouse model where treatment with a combination of antibodies has been shown to control HIV replication (*Nature*, 2012, 492(7427): 118-22). Humanized mice are first generated by reconstituting $NOD.RAG1^{-/-}$. $IL\gamma^{-/-}$ mice with human fetal liver-derived CD34+ hematopoietic stem cells. These mice have a completely human immune system, can be infected by HIV and do not negatively react to human antibodies. Infected control mice are compared with mice receiving either neutralizing antibody cocktail alone or in combination with either human immune effector cells along with the Adapter-like ADCC Enhancer of the present invention. The mice receiving the ADCC Enhancer show sustained reduction in viremia and recovery in T cell numbers.

An alternate model system to test the clinical efficacy of the ADCC Enhancer is the simian-human immunodeficiency virus (SHIV)-infected infant rhesus macaque model where neutralizing antibodies have been shown to prevent rapid onset of the disease (Jaworski et al. *J Virol.* 2013, 87(19): 10447-59). Infected control macaques are compared with those receiving either neutralizing antibody cocktail alone or in combination with the Adapter-like ADCC Enhancer of the present invention. The macaques receiving the ADCC enhancer similarly show sustained reduction in viremia and recovery in T cell numbers.

DNA and RNA constructs that encode ADCC Enhancing system of the present invention may be formulated for administration to a subject using techniques known to the skilled artisan. Formulations comprising DNA and RNA constructs that encode the ADCC Enhancing system may include pharmaceutically acceptable excipient(s). Excipients included in the formulations will have different purposes depending, for example, on the kind of gene construct or effector cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

In another embodiment of the invention, a pharmaceutical formulation of the Adapter-like ADCC Enhancer of the invention is administered into the patient. Exemplary administration modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration. As used herein, the terms "treat", "treating", and "treatment" have their ordinary and customary meanings, and include one or more of: blocking, ameliorating, or decreasing in severity and/or frequency a symptom of a disease (e.g., cancer) in a subject, and/or inhibiting the growth, division, spread, or proliferation of cancer cells, or progression of cancer (e.g., emergence of new tumors) in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

The clinical potency, both as a therapeutic and a prophylactic, of the ADCC Enhancer of the present invention may be optionally enhanced through the use of dendritic cells (DCs). In lymphoid organs, DCs present antigen to T-helper cells, which in turn, regulate immune effectors including CTLs, B cells, macrophages, eosinophils and NK cells. It has been reported that autologous DC engineered to express an HIV antigen or pulsed with exogenous HIV protein was able to prime CTLs in vitro against HIV (Wilson et al., J Immunol., 1999, 162:3070-78). Therefore, in an embodiment of the present invention, DCs are first isolated from the subject patient, and then primed ex vivo through incubation with a source of target antigen(s), e.g., certain tumors-associated antigens or other surface markers of a disease which can be from the subject patient or a foreign source. These DCs are eventually infused back into the patient prior to treatment by autologous CTL and/or other effector cells transfected with the ADCC Enhancing system of the present invention or by formulations comprising DNA and RNA constructs that encode the ADCC Enhancing system. This provides a model of enhanced treatment as well as vaccine using the ADCC Enhancer with the help of DCs.

The invention also provides a kit comprising one or more containers filled with quantities of gene constructs encoding the Adapter-like ADCC Enhancer, with pharmaceutically acceptable excipients. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

IV. Examples (1) T cell Adapter Construction

According to various embodiments of the present invention, Adapter-like ADCC Enhancers, i.e., fusion proteins with a high-affinity Fc-binding domain linked to a high-affinity CD3-binding domain were developed and tested.

Specifically, a synthetic CD64-dhOKT3 DNA was first generated through chemical synthesis as the genetic material for producing an Adapter-like ADCC Enhancer (or, a soluble, free-associating, circulating T-cell adapter) where the Fc-binding ectodomain of CD64 is fused to a de-immunized and humanized scFv version of ORTHOCLONE OKT3 (also known as Muromonab-CD3), which is an anti-CD3 antibody.

Other Fc-binding domains, e.g., based on the ectodomains, i.e., extracellular domains, of other Fc receptors (e.g., CD32 and CD16), can also be used in other embodiments of the invention. However, CD64 (i.e., FcγRI) has about a 100- to a 1000-fold higher affinity for the Fc region of antibodies than CD16, making CD64's ectodomain, the part of CD64 that is responsible for antibody binding, the preferred candidate for the Fc-binding domain in the fusion protein.

The junctions of the protein fusion were decided by the exon boundaries of the original protein (see FIG. 2). The CD64 domain thus derived for the fusion protein included two exons coding for the secretory signal followed by three exons coding for the ectodomain and is shown in FIG. 3 as SEQ ID NO:1. The secretory signal sequence does not have to come from CD64, however, and can be replaced by other suitable secretory signal sequences. Moreover, in an alternative embodiment, the junctions of the protein fusion are based on the predicted amino acid boundary between the ectodomain and the transmembrane domain of the original protein. Compared to the exon-based fusion, this approach would add to the fusion protein portions of the linker sequence between the two original domains for instance.

The rest of the fusion protein (SEQ ID NO:2), including two spacer sequences and the OKT3 sequence is shown in FIG. 4. The OKT3 is originally derived from mouse cells, but has been humanized, i.e., converted or mutated to be more like an antibody from humans by many groups. Humanizing an antibody or antibody fragment is a standard procedure known to one of ordinary skills in the art. The complete sequence (SEQ ID NO:3) of the Adapter-like ADCC Enhancer where the extracellular portion of CD64 was fused with a de-immunized and humanized OKT3 (dhOKT3) through a flexible serine-glycine linker is shown in FIG. 5. In alternative embodiments, other agonistic anti-CD3 sequences such as a humanized TR66, can be used.

Referring now to FIG. 6, the CD64-dhOKT3 fusion protein was back translated and sequence-optimized to generate the DNA sequence (SEQ ID NO.4) shown in the figure. The optimization relied on a combination of choosing codons for individual amino acids that appear in humans more frequently as well as removing repeat regions as well as regions that could potentially form secondary structures.

Alternate embodiments of the invention include adding a tag (e.g., Myc or His) to ease purification. Another option would be to make the tag cleavable so that the purified protein can be used in therapy without interference from the tag. Both embodiments can be practiced using standard procedures well known to one of ordinary skills in the art and are not detailed here.

(2) Expression and Purification

Figure 8:
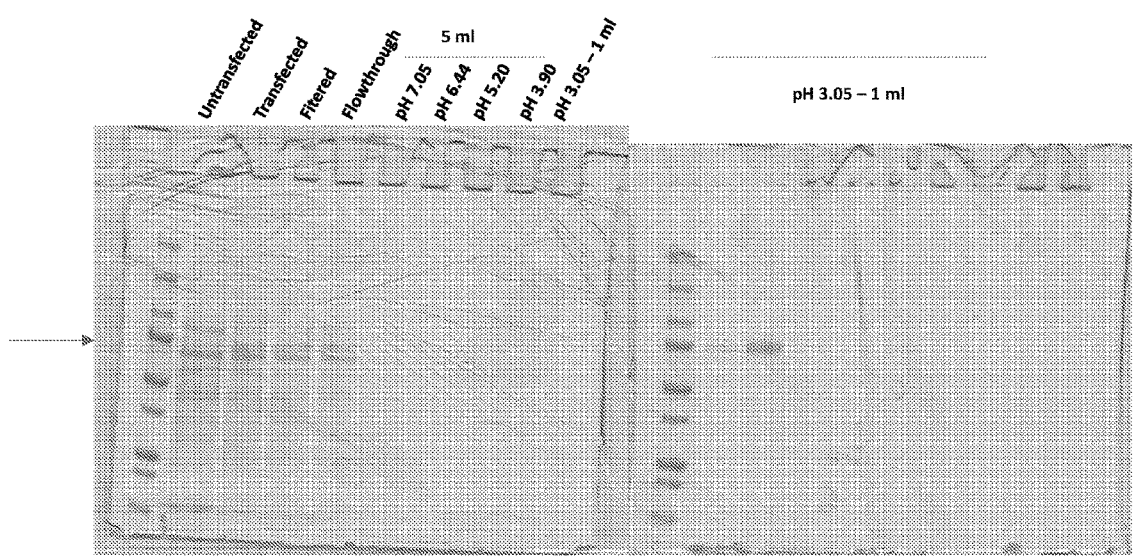
FIG. 8 are photographic images of coomasie-stained gels that illustrate purification of soluble ADCC Enhancer using a commercial human IgG column (GE Life Sciences). Transfected cells were completely removed from the culture supernatant through multiple centrifugation steps followed by ultrafiltration. The column was equilibrated in a neutral buffer and the supernatant was loaded, followed by the flow-through (to ensure complete binding). The protein was purified through a step-wise gradient of decreasing pH. The purified protein was immediately neutralized in high molarity alkaline Tris buffer. The purified protein was exchanged into PBS either by sequential dialysis or by repeated ultra-filtration through an Amicon® Ultra Centrifugal filters. Lanes in the gel on the right side represent various elution fractions when the washing buffer is at pH 3.05.

The synthetic gene for the CD64-dhOKT3 fusion protein was chemically synthesized and cloned into a mammalian expression vector. The vector pVITRO2-MCS, commercially available from Invivogen®, was used, but there are many common vectors that can serve the same function. For expression, the recombinant expression vector was transfected into Expi293 cells (commercially available from Thermo Fisher Scientific) following the manufacturer's instructions. The resulting cell line produced soluble secreted protein (FIGS. 7 and 8). Briefly, Expi293 cells were grown in Expi293 Expression media and transfected using EXPIFECTAMINE 293 Transfection Reagent. Synthesized ADCC-enhancers 1 and 2 (FIG. 7) were added to the culture 16-20 hours post-transfection and the supernatant was collected 2 to 7 days post-transfection. In alternate embodiments of the invention, other expression systems, e.g., CHO cells, are used. In an alternate embodiment, the expression cassette can be stably integrated into the genome of the cell line to generate a stable derivative that produces the fusion protein.

The ADCC-enhancer protein was affinity-purified using commonly known methods such as commercially available IgG SEPHAROSE column (GE Healthcare Life Sciences) (FIG. 8). Briefly, supernatant from transfected cells was loaded onto the column packed with SEPHAROSE beads crosslinked with human IgG. The column was then washed with a neutral pH buffer and a step-wise gradient of lower pH citrate-phosphate buffer. The ADCC-enhancer protein was eluted at low pH (~pH 3) and immediately neutralized in 1M TrisHCl (pH 7.4). The buffer was exchanged by dialysis or ultrafiltration.

Other standard purification methods like desalting columns could also be used. Another alternate embodiment uses a Protein L based affinity column. Protein L binds to the kappa chain of many species including that of an scFv, such as the OKT3 portion of the fusion protein here. Other standard methods for purifying an untagged protein, e.g., ion exchange, size exclusion, and so on, can also be used either alone or in combination in the present invention. Alternatively and as mentioned before, the fusion protein can be tagged with standard tags for easy purification using appropriate affinity columns. These steps can also be used in tandem to yield higher purity protein.

(3) Binding Affinity

Figure 9:
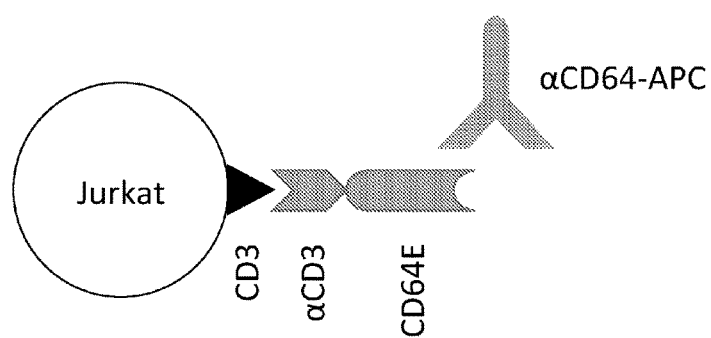
FIG. 9 schematically depicts an assay using Jurkat cells to test the ability of an Adapter-like ADCC Enhancer of the present invention to bind $CD3^+$ immune effector cells.

The ability of the CD64-antiCD3 fusion protein to bind Fc and CD3 can be tested either directly using the supernatant or the purified protein in several ways. For instance, as shown in FIG. 9, Jurkat cells can be used to test such affinity, as Jurkat cells are T lymphocyte cells expressing CD3.

Figure 10:
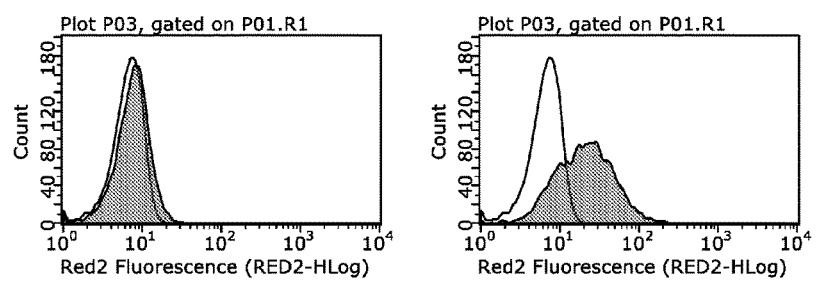
FIG. 10 illustrates FACS data showing, in an assay according to FIG. 9, the binding between Jurkat cells and the ADCC Enhancer of the invention before purification ("Sample Load") and after purification ("Purified Protein"). The unfilled curve represents the negative control. Here and in all subsequent experiments, purified ADCC Enhancer is used at 10-20 ng/microliter unless noted otherwise.
Figure 11:
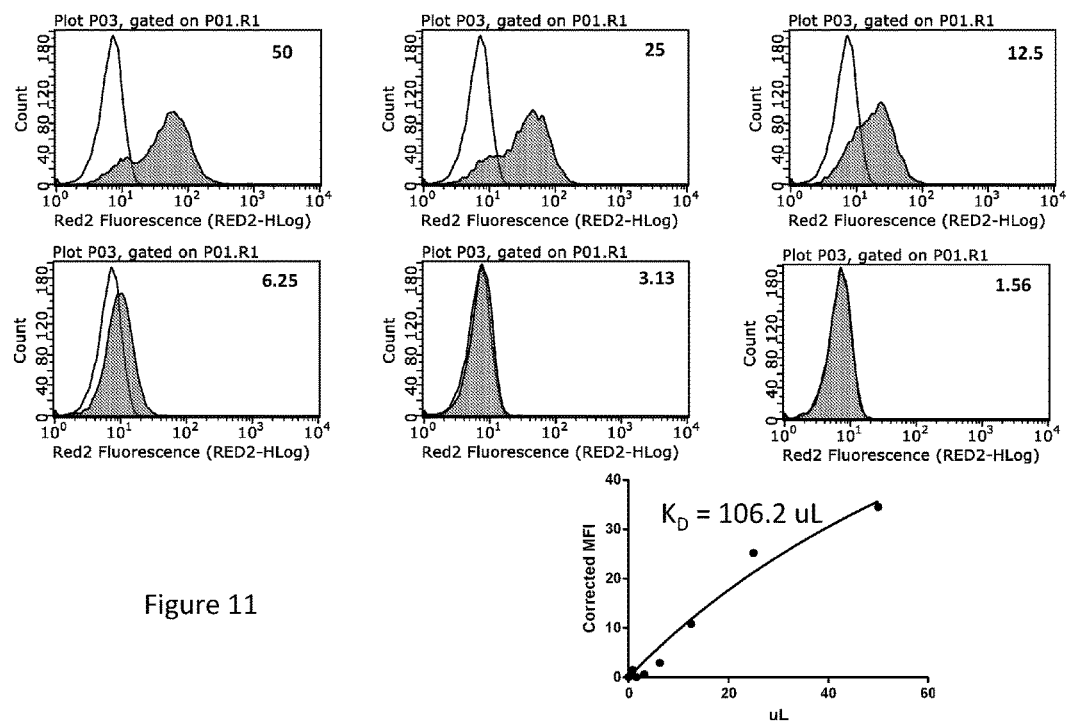
FIG. 11 illustrates FACS data showing titration of binding between Jurkat cells and the ADCC Enhancer of the invention at various concentrations. The volume of the Enhancer in microliters are indicated in the upper right corner of the top six diagrams as: 50, 25, 12.5, 6.25, 3.13 and 1.56 microliters. The bottom diagram summarizes the data. $CD3^+$ Jurkat cells were incubated with various amounts of the Enhancer, excess Enhancer was removed by washing the cells in PBS, and bound Enhancer proteins were detected using fluorescent anti-human CD64 antibody.

According to one example, 2×10⁵ Jurkat cells were washed in PBS and incubated for 30 minutes at 4° C. in 50 μl of culture supernatant (from Expi293 cells that had been transfected for several days with the expression vector) or purified fusion proteins. The cells were washed twice with PBS and then bound ADCC enhancer was detected using commercially available fluorescently tagged anti-CD64 antibody (FIG. 10). In FIG. 11, titration of binding to Jurkat cells was conducted and results show correlation between binding and the concentration of the Enhancer.

Figure 12:
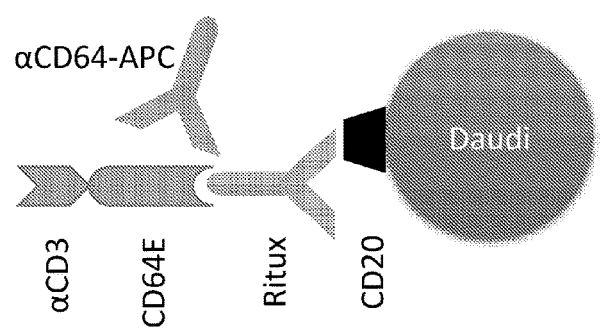
FIG. 12 schematically depicts an assay using Daudi cells to test the ability of an Adapter-like ADCC Enhancer of the present invention to bind CD20+ target cells coated with RITUXAN (rituximab).
Figure 13:
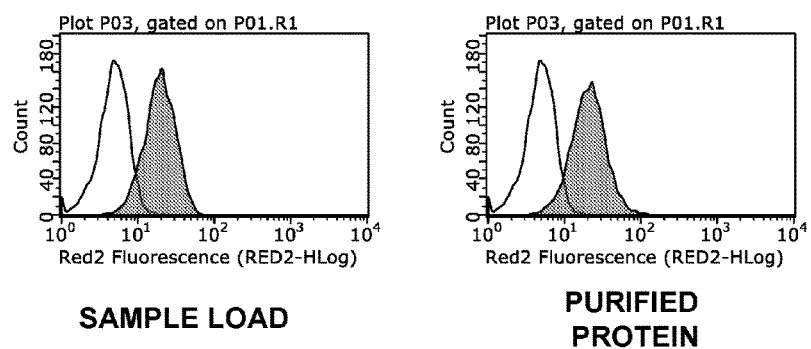
FIG. 13 illustrates FACS data showing, in an assay according to FIG. 12, the binding between Daudi cells and the ADCC Enhancer of the invention before purification ("Sample Load") and after purification ("Purified Protein").
Figure 14:
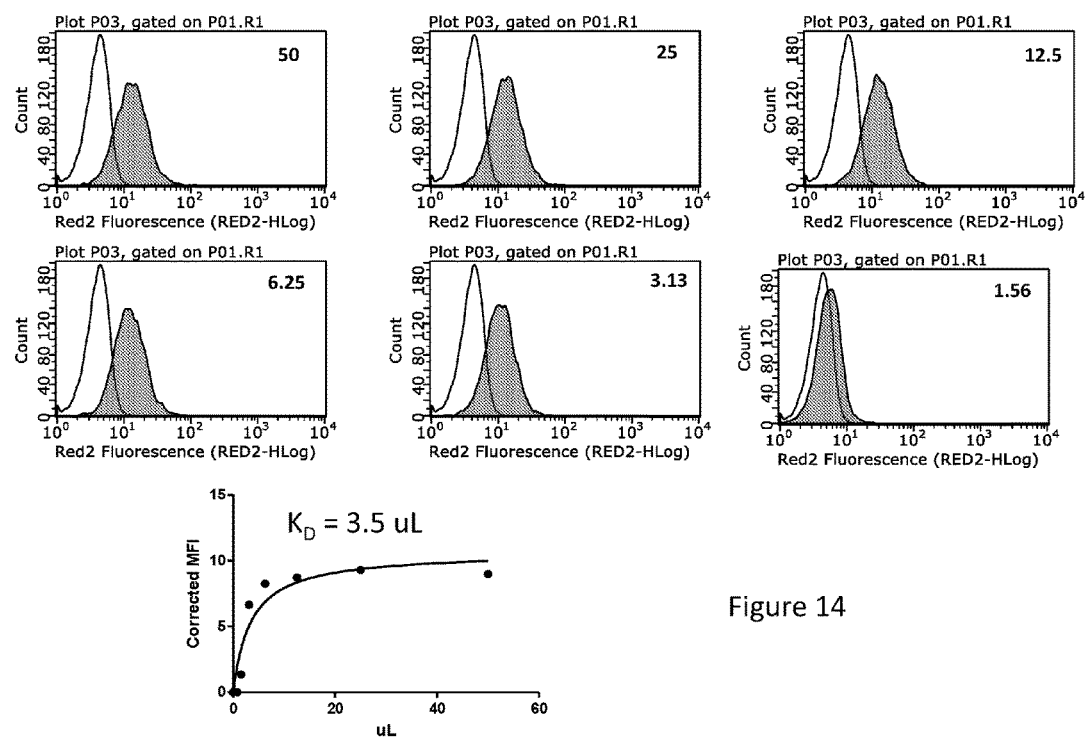
FIG. 14 illustrates FACS data showing titration of binding between Daudi cells and the ADCC Enhancer of the invention at various concentrations. The volume of the Enhancer in microliters are indicated in the upper right corner of the top six diagrams as: 50, 25, 12.5, 6.25, 3.13 and 1.56 microliters. The bottom diagram summarizes the data. CD20+ Daudi cells were coated with RITUXAN (rituximab) (anti-CD20 antibody) and excess RITUXAN (rituximab) was removed by washing the cells with PBS. RITUXAN (rituximab)-coated cells were incubated with various amounts of the Enhancer, and excess Enhancer was removed by washing the cells in PBS. Bound Enhancer proteins were detected using fluorescent anti-human CD64 antibody. There was approximately 30-fold higher affinity for the antibody observed in the ADCC Enhancer compared to CD20.

With tagged protein, binding affinity can also be detected using a fluorescently tagged anti-tag antibody. This approach can also be used to detect binding of the CD64 domain by rituximab-coated CD20⁺ Daudi cells (see FIG. 12). Briefly, 10⁶ Daudi cells were harvested, washed with PBS and incubated for 30 minutes at 4° C. with 0.1 μg/ml of rituximab (an antibody against CD20, also known as RITUXAN. MABTHERA and ZYTUX). Cells were again washed in PBS and then incubated with the supernatant or purified protein as described above (FIG. 13). In FIG. 14, titration of binding to Daudi cells was conducted and results show very correlation between binding and the concentration of the Enhancer. In fact, the Fc- or antibody-binding by the Adapter-like ADCC Enhancer appear to be about 30 times stronger than CD3-binding from the other end of the Enhancer.

In alternate embodiments, heterologous aggregation is examined between rituximab-coated Daudi and Jurkat cells in co-culture systems as indication of binding affinities. Daudi and Jurkat cells are respectively labeled with live cell stains such as CFSE or Cell Trace Far Red using standard methods and/or engineered to express fluorescent proteins such as GFP. The cells are then co-incubated with the Rituximab and the soluble ADCC Enhancer of the present invention. FACS data is examined for doublets that are positive for both colors. As one of ordinary skill readily understands, the choices of cell lines in embodiments described herein are not limited to Jurkat and Daudi cells—the present invention contemplates the use of a variety of cell lines or primary cells in combination with appropriate antibodies.

The ability of the CD64-antiCD3 fusion protein to bind Fc and CD3 can also be tested by surface plasmon resonance, or other standard biochemical or cell-based assays.

(4) Cytotoxicity Enhancement

Naïve primary CD8⁺ T cells were isolated from donated blood using standard procedure, e.g., using ROSETTESEP CD8 T Cell Enrichment Kit (Stem Cell Technology) followed by expansion with anti-CD3/CD28. Alternatively, similar experiments can be conducted with total T cells or PBMCs. Using any one of these cells, the ability of the Enhancer of the invention to cause activation, proliferation and for triggering cytotoxicity, in particular, ADCC, was tested. Specifically, T cell proliferation can be measured by flow cytometry or other traditional methods e.g. thymidine incorporation, CFSE dilution, etc. Activation can be measured by detecting a variety of known activation markers e.g. HLA-DR, CD25, CD69, etc. Typically, for these experiments, the Enhancer might work by itself but additional experiments were done with or without:

(A) 50 IU/ml of IL-2;
(B) Target cells; and/or
(C) Appropriate antibodies.

When including target cells, they can be pretreated with mitomycin C to stall proliferation and minimize the effects of overcrowding. Also, Lysosomal-associated membrane protein-1 (LAMP-1 or CD107a) has been described as a marker of CD8+ T-cell and NK cell degranulation of lytic granules following stimulation. Therefore, in the co-culture experiments described above, the level of CD107a+ T cells can be analyzed as a measure of degranulation through flow cytometry.

To assess cytotoxicity, T cells were co-cultured for one or two days with CellTrace-tagged target cells in the presence of an appropriate therapeutic antibody. Results and setup of several examples are shown in FIGS. 15-23, and provides overwhelming evidence of the Adapter-like Enhancer's ability to trigger, enhance or amplify antibody-dependent cytotoxicity against a variety of cancer cells. Data presented in these figures involves effective killing of B lymphoblast cells (Daudi and Raji), breast cancer cells (SK-BR3 and MDA-MB-231) and cells expressing PD-1 (293-PD1).

Figure 15:
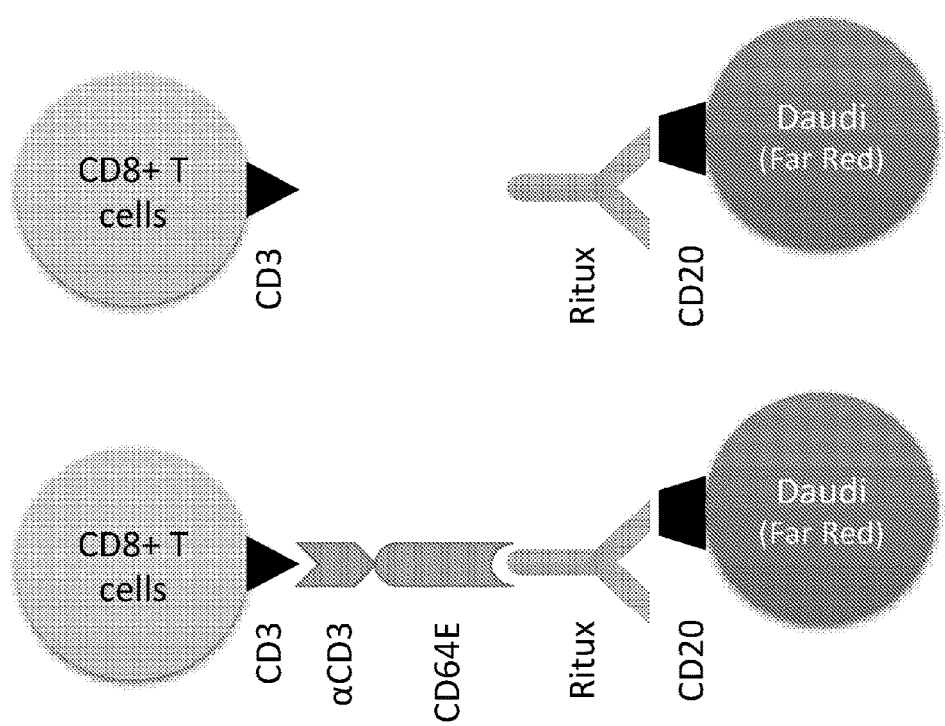
FIG. 15 schematically depicts an assay using Daudi cells coated with RITUXAN (rituximab), and CD8+ T cells to test the ability of an Adapter-like ADCC Enhancer of the present invention to mediate and amplify cytotoxicity against target cancer cells.
Figure 16:
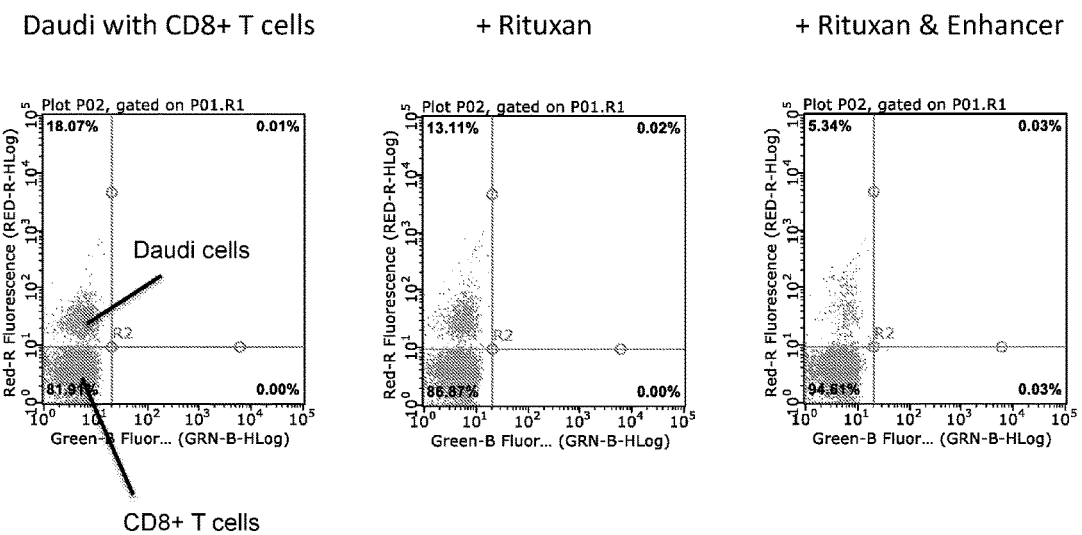
FIG. 16 illustrates FACS data showing detection of the target (Daudi) cells (top cluster) and the effector T cells (bottom cluster), in an assay according to FIG. 15. The data indicates that the Enhancer of the invention was able to recruit the T cells to lyse much of the Daudi cell population without diminishing T cell viability (right diagram). In this and all subsequent experiments, E:T (effector cell to target cell) ratio was 10.
Figure 17:
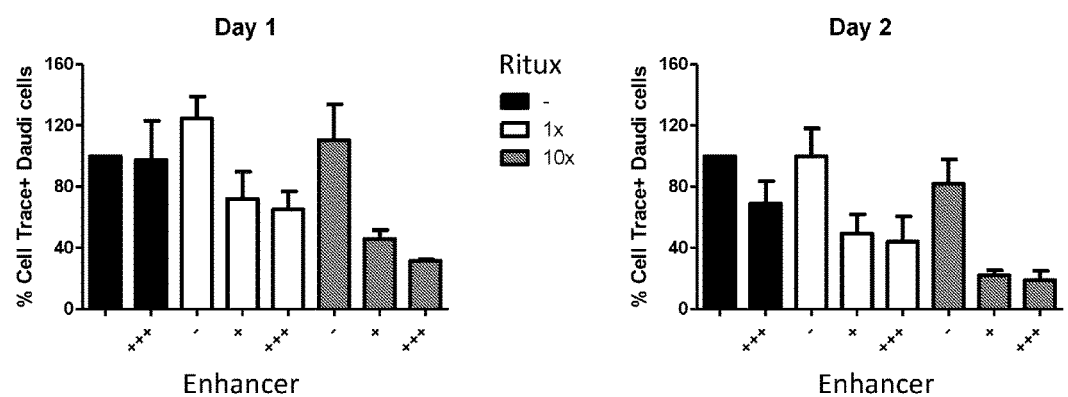
FIG. 17 illustrates data from cytotoxicity experiments involving two concentrations of RITUXAN (rituximab) (anti-CD20), CD20+ Daudi cells, CD8+ T cells and the Enhancer of the invention. The data shows that the Enhancer increased T cell's killing of the target cells, and that the killing was dependent on both RITUXAN (rituximab) and Enhancer concentrations. As the data between Day 1 and Day 2 indicates, there was also increased killing at longer exposure (time-dependent ADCC). RITUXAN (rituximab) was used at 0.1 µg/ml (10×) or 0.01 µg/ml (1×). Enhancer was used at 12.5 microliter (+) or 50 microliter (+++).
Figure 18:
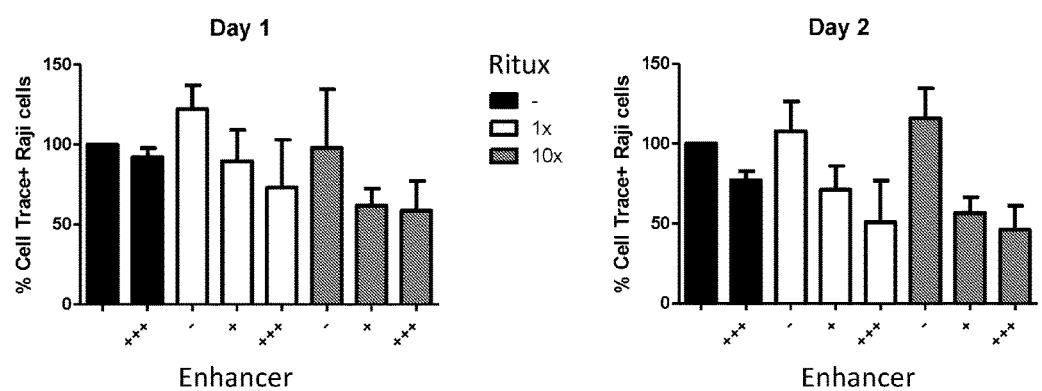
FIG. 18 illustrates data from cytotoxicity experiments involving two concentrations of RITUXAN (rituximab), Raji cells, CD8+ T cells and the Enhancer of the invention. The data shows similar results as in FIG. 17 at the same concentrations of RITUXAN (rituximab) and Enhancer.
Figure 19:
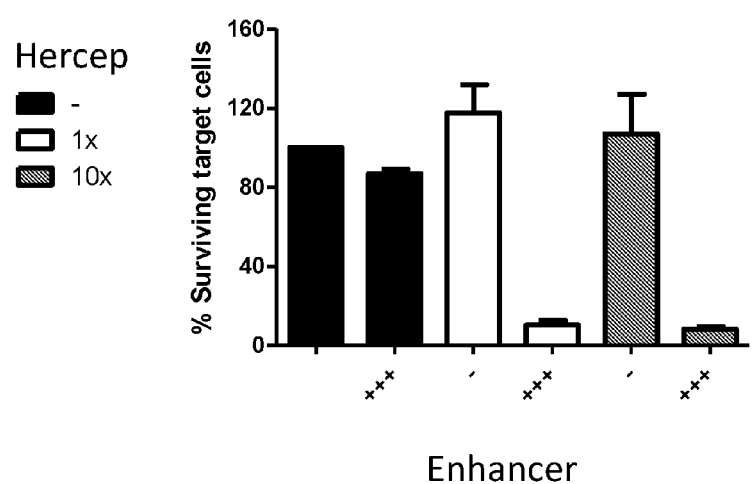
FIG. 19 illustrates data from cytotoxicity experiments involving two concentrations of HERCEPTIN (trastuzumab), HER+SK-BR3 cells, CD8+ T cells and the Enhancer of the invention. The data shows even more pronounced cytotoxic effect (compared to results in FIG. 18) when the Enhancer was added. HERCEPTIN (trastuzumab) was used at 1 µg/ml (10×) or 0.1 µg/ml (1×). Enhancer was used at 50 microliter (+++).
Figure 20:
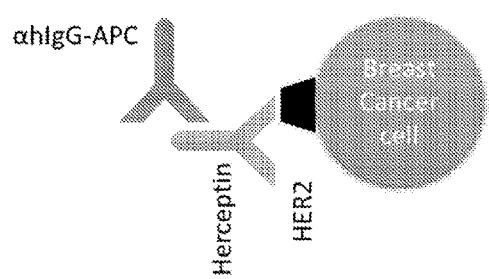
FIG. 20 schematically depicts how HER2 expression was measured in different breast cancer cells according to an example of the invention.
Figure 21:
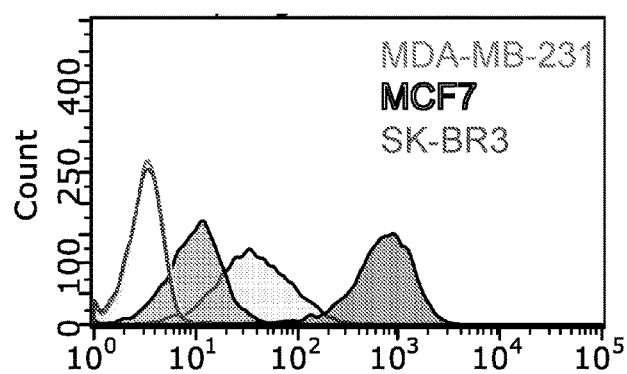
FIG. 21 compares HER2 expression levels among three different breast cancer lines: MDA-MB-231, MCF7, and SK-BR3. The far left peak represents unstained control, followed by peaks of MDA-MB-231, MCF7, and SK-BR3 cells, respectively. The data shows that among the three, SK-BR3 has the highest HER2 expression level while MDA-MB-231 has the lowest.
Figure 22:
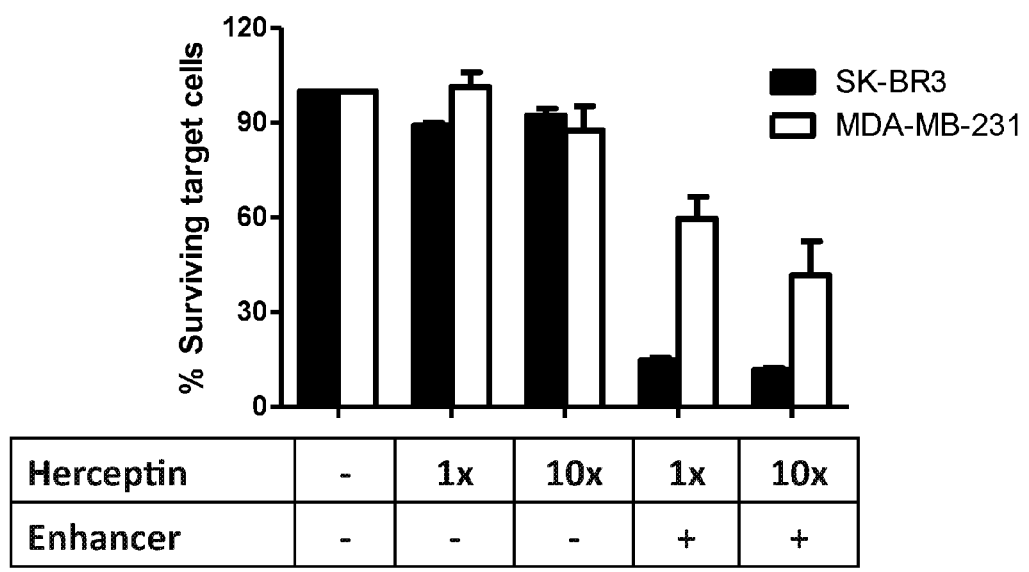
FIG. 22 illustrates data from cytotoxicity experiments involving HERCEPTIN (trastuzumab), HER-hi SK-BR3 cells, HER-lo MDA-MB-231 cells, and the Enhancer of the invention. The data shows the Enhancer's ability to amplify HERCEPTIN (trastuzumab)'s killing capacity in both types of breast cancer cells. The data also shows more marked effect in SK-BR3 cells, indicating that the effect is dependent on the expression level of HER2. However, the ability to kill MDA-MB-231 cells shows that the Enhancer of the invention can be used to sensitize even low HER2-expressing tumors to HERCEPTIN (trastuzumab). Enhancer was used at 50 microliter in these experiments.

For example, data and mechanism presented in FIGS. 15 and 16 show that the Enhancer of the invention was able to kill much of the CD20⁺ Daudi cell population, in the presence of RITUXAN (rituximab), by recruiting T cell to affect ADCC. As another example, data presented in FIG. 19 shows that the Enhancer of the invention triggers the killing capacity of HERCEPTIN (trastuzumab), an antibody designed against HER2 receptors on breast cancer cells, over SK-BR3 breast cancer cells presumably as T cells were recruited by the Enhancer to enhance ADCC.

Additional testing can be performed with other antibodies in other cancer lines and settings, for example: (a) CD33+ AML lines (e.g. HL-60, MOLM-13 and THP-1) treated with anti-CD33 antibody (WM-53); (b) CD19+ lines (e.g. NALM-6 and MEC-1) treated with anti-CD19 antibody (HIB19); and (c) EpCAM+ lines (e.g. SW480) treated with anti-EpCAM antibody (HEA-125).

Figure 23:
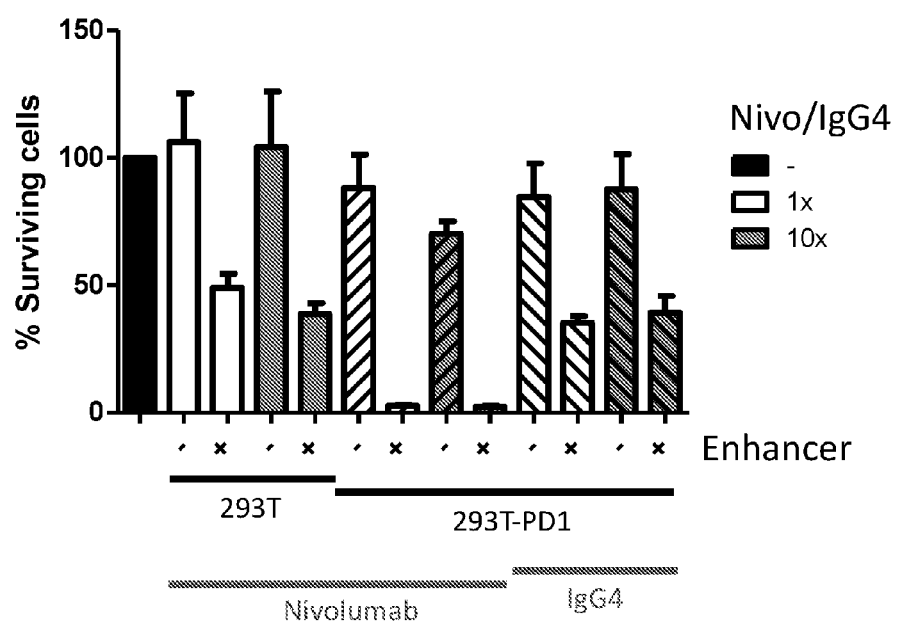
FIG. 23 illustrates data from cytotoxicity experiments involving Nivolumab (anti-PD1), HEK-293T cells that have transgenically expressed PD1 ("293T-PD1"), CD8+ T cells, and the Enhancer of the invention. The parental, unmodified HEK-293T cells ("293T") as well as an IgG4 control were included as controls. Significant target cell lysis was seen only when cells expressing PD-1 were exposed to Nivolumab in the presence of the Enhancer. CD8+ T cells were in all the samples depicted including the far left control.

Referring now to FIG. 23, cytotoxicity experiments involving Nivolumab (anti-PD1 antibody), HEK-293T cells (Human Embryonic Kidney cells expressing large T antigen) that have transgenically expressed PD1 ("293T-PD1"), CD8+ T cells, and the Enhancer of the invention. The parental, unmodified HEK-293T cells ("293T") as well as an IgG4 control were included as controls. Nivolumab was developed as an IgG4 antibody so as to not have any ADCC activity. However, subsequent experiments have shown that ADCC and PD1 antibodies might work better together. Unlike CD16, CD64 has the ability to bind IgG4 and convert originally ADCC-negative, antibodies, such as Nivolumab, to ADCC-positive ones in order to recruit additional help from other immune effector cells such as T cells. As shown in the figure, by itself, Nivolumab, even when its concentration is increased by 10 times, still had only limited killing capacity over the target 293T-PD1 cells-showing about 75% target survival. However, when the Adapter-like Enhancer of the invention was added to the mix, the target cell survival rate plummeted to less than 5%. This provides the basis for promising therapeutic uses of the Enhancer of the invention in combination or conjunction with IgG4 antibodies or other immune effector cells that do not otherwise possess ADCC capability.

The data contained herein support the use of the Adapter-like ADCC Enhancer with antibodies, such as RITUXAN (rituximab) and HERCEPTIN (trastuzumab), to enhance their function, to reduce antibody dosage, reduce side effects and anti-antibody response.

This works not only in treating cancer but also in treating autoimmunity. For example, RITUXAN or Rituximab has produced mixed results in treating autoimmune patients: it works well in RA but only marginally in SLE. One reason for this is that macrophage-mediated B cell depletion is saturated in SLE patients. Redirecting B cell killing to T cells using the ADCC Enhancer as a T-cell Adapter will circumvent this problem.

Further, the Enhancer can be used in patients with low affinity version of CD16 (158F), or patients where ADCC/CDC is suppressed somehow, e.g., chronic lymphocytic leukemia (CLL) patients and other patients undergoing cancer treatment.

There are many antibodies where the role of ADCC was not appreciated until the antibodies were already in the clinic, e.g. e.g. trastuzumab, anti-PD-1, anti-PD-L1, anti-CTLA4, etc. Many of these antibodies are IgG4 antibodies. As seen above, the CD64 part of the enhancer can bind IgG4 and convert originally ADCC-negative antibodies to ADCC-positive ones as shown above.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

The invention claimed is:

1. A fusion protein, comprising a binding domain for an antibody's Fc fragment ("Fc-binding domain"), and a binding domain for CD3 ("CD3-binding domain"), wherein said Fc-binding domain comprises the ectodomain of CD64, and wherein said CD3-binding domain comprises an scFv comprising the variable light (VL) and variable heavy (VH) chains of an OKT3 monoclonal antibody, wherein said OKT3 monoclonal antibody is a dhOKT3 (deimmunized, humanized OKT3).

2. A pharmaceutical composition comprising the fusion protein of claim 1, and a pharmaceutically acceptable excipient.

3. The fusion protein of claim 1, wherein said ectodomain of CD64 is fused with said scFv of dhOKT3 through a flexible serine-glycine linker consisting of multiple units of serine residues and glycine residues.

4. The fusion protein of claim 3, wherein the amino acid sequence of said ectodomain of CD64 is SEQ ID NO:1.

5. A fusion protein, wherein said fusion protein comprises the amino acid sequence of SEQ ID NO:3.

6. The fusion protein of claim 3, wherein the amino acid sequence of said flexible serine-glycine linker and said scFv of dhOKT3 is SEQ ID NO:2.

* * * * *

SEQUENCE LISTING

```
<160> NUMBER OF SEQ ID NOS: 4

<210> SEQ ID NO 1
<211> LENGTH: 281
<212> TYPE: PRT
<213> ORGANISM: Homo sapiens

<400> SEQUENCE: 1

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255
```

```
Leu Tyr Trp Cys Glu Ala Ala Thr Glu Asp Gly Asn Val Leu Lys Arg
            260                 265                 270

Ser Pro Glu Leu Glu Leu Gln Val Leu
        275                 280

<210> SEQ ID NO 2
<211> LENGTH: 250
<212> TYPE: PRT
<213> ORGANISM: Artificial
<220> FEATURE:
<223> OTHER INFORMATION: Linker sequences with a humanized OKT3 sequence

<400> SEQUENCE: 2

Ser Ser Gly Gly Gly Ser Gln Val Gln Leu Val Gln Ser Gly Gly
1               5                   10                  15

Gly Val Val Gln Pro Gly Arg Ser Leu Arg Leu Ser Cys Lys Ser Ser
            20                  25                  30

Gly Tyr Thr Phe Thr Arg Tyr Thr Met His Trp Val Arg Gln Ala Pro
        35                  40                  45

Gly Lys Gly Leu Glu Trp Ile Gly Tyr Ile Asn Pro Ser Arg Gly Tyr
    50                  55                  60

Thr Asn Tyr Asn Gln Lys Val Lys Asp Arg Phe Thr Ile Ser Arg Asp
65                  70                  75                  80

Asn Ser Lys Asn Thr Ala Phe Leu Gln Met Asp Ser Leu Arg Pro Glu
                85                  90                  95

Asp Thr Gly Val Tyr Phe Cys Ala Arg Tyr Tyr Asp Asp His Tyr Cys
            100                 105                 110

Leu Asp Tyr Trp Gly Gln Gly Thr Pro Val Thr Val Ser Ser Val Glu
        115                 120                 125

Gly Gly Ser Gly Gly Ser Gly Ser Gly Ser Gly Gly Val Asp
    130                 135                 140

Asp Ile Gln Met Thr Gln Ser Pro Ser Ser Leu Ser Ala Ser Val Gly
145                 150                 155                 160

Asp Arg Val Thr Ile Thr Cys Arg Ala Ser Ser Ser Val Ser Tyr Met
                165                 170                 175

Asn Trp Tyr Gln Gln Thr Pro Gly Lys Ala Pro Lys Arg Trp Ile Tyr
            180                 185                 190

Asp Thr Ser Lys Val Ala Ser Gly Val Pro Ser Arg Phe Ser Gly Ser
        195                 200                 205

Gly Ser Gly Thr Asp Tyr Thr Phe Thr Ile Ser Ser Leu Gln Pro Glu
    210                 215                 220

Asp Ile Ala Thr Tyr Tyr Cys Gln Gln Trp Ser Ser Asn Pro Leu Thr
225                 230                 235                 240

Phe Gly Gln Gly Thr Lys Leu Gln Ile Thr
                245                 250

<210> SEQ ID NO 3
<211> LENGTH: 531
<212> TYPE: PRT
<213> ORGANISM: Artificial
<220> FEATURE:
<223> OTHER INFORMATION: fusion protein sequence for an Adapter-Like
      ADCC Enhancer embodiment

<400> SEQUENCE: 3

Met Trp Phe Leu Thr Thr Leu Leu Leu Trp Val Pro Val Asp Gly Gln
1               5                   10                  15
```

-continued

```
Val Asp Thr Thr Lys Ala Val Ile Thr Leu Gln Pro Pro Trp Val Ser
             20                  25                  30

Val Phe Gln Glu Glu Thr Val Thr Leu His Cys Glu Val Leu His Leu
         35                  40                  45

Pro Gly Ser Ser Ser Thr Gln Trp Phe Leu Asn Gly Thr Ala Thr Gln
     50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
             100                 105                 110

Val Phe Thr Glu Gly Glu Pro Leu Ala Leu Arg Cys His Ala Trp Lys
         115                 120                 125

Asp Lys Leu Val Tyr Asn Val Leu Tyr Tyr Arg Asn Gly Lys Ala Phe
     130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                 165                 170                 175

Thr Ser Ala Gly Ile Ser Val Thr Val Lys Glu Leu Phe Pro Ala Pro
             180                 185                 190

Val Leu Asn Ala Ser Val Thr Ser Pro Leu Leu Glu Gly Asn Leu Val
         195                 200                 205

Thr Leu Ser Cys Glu Thr Lys Leu Leu Leu Gln Arg Pro Gly Leu Gln
     210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                 245                 250                 255

Leu Tyr Trp Cys Glu Ala Ala Thr Glu Asp Gly Asn Val Leu Lys Arg
             260                 265                 270

Ser Pro Glu Leu Glu Leu Gln Val Leu Ser Ser Gly Gly Gly Gly Ser
         275                 280                 285

Gln Val Gln Leu Val Gln Ser Gly Gly Val Val Gln Pro Gly Arg
     290                 295                 300

Ser Leu Arg Leu Ser Cys Lys Ser Ser Gly Tyr Thr Phe Thr Arg Tyr
305                 310                 315                 320

Thr Met His Trp Val Arg Gln Ala Pro Gly Lys Gly Leu Glu Trp Ile
                 325                 330                 335

Gly Tyr Ile Asn Pro Ser Arg Gly Tyr Thr Asn Tyr Asn Gln Lys Val
             340                 345                 350

Lys Asp Arg Phe Thr Ile Ser Arg Asp Asn Ser Lys Asn Thr Ala Phe
         355                 360                 365

Leu Gln Met Asp Ser Leu Arg Pro Glu Asp Thr Gly Val Tyr Phe Cys
     370                 375                 380

Ala Arg Tyr Tyr Asp Asp His Tyr Cys Leu Asp Tyr Trp Gly Gln Gly
385                 390                 395                 400

Thr Pro Val Thr Val Ser Ser Val Glu Gly Ser Gly Gly Ser Gly
                 405                 410                 415

Gly Ser Gly Gly Ser Gly Gly Val Asp Asp Ile Gln Met Thr Gln Ser
             420                 425                 430

Pro Ser Ser Leu Ser Ala Ser Val Gly Asp Arg Val Thr Ile Thr Cys
```

```
                     435                 440                 445
Arg Ala Ser Ser Val Ser Tyr Met Asn Trp Tyr Gln Gln Thr Pro
    450                 455                 460

Gly Lys Ala Pro Lys Arg Trp Ile Tyr Asp Thr Ser Lys Val Ala Ser
465                 470                 475                 480

Gly Val Pro Ser Arg Phe Ser Gly Ser Gly Ser Gly Thr Asp Tyr Thr
                    485                 490                 495

Phe Thr Ile Ser Ser Leu Gln Pro Glu Asp Ile Ala Thr Tyr Tyr Cys
                500                 505                 510

Gln Gln Trp Ser Ser Asn Pro Leu Thr Phe Gly Gln Gly Thr Lys Leu
            515                 520                 525

Gln Ile Thr
530

<210> SEQ ID NO 4
<211> LENGTH: 1596
<212> TYPE: DNA
<213> ORGANISM: Artificial
<220> FEATURE:
<223> OTHER INFORMATION: DNA sequence for a fusion protein embodiment

<400> SEQUENCE: 4
atgtggtttc tgactacact gctgctgtgg gtgcccgtgg atggacaggt ggatactaca      60
aaagccgtga ttacactgca gccccttggt gtgtctgtct tccaggagga aaccgtgaca     120
ctgcactgcg aggtcctgca tctgccaggc agctcctcta cccagtggtt tctgaacgga     180
actgctaccc agacatctac tcccagttac cgcatcacaa gcgcatccgt gaatgacagc     240
ggcgagtatc gatgccagcg ggggctgtca ggtcgaagcg atccaatcca gctggaaatt     300
caccggggggt ggctgctgct gcaggtgagt tcaagggtct tcaccgaggg tgaaccctg     360
gcactgaggt gtcacgcctg aaggacaaa ctggtgtaca acgtcctgta ctatagaaat     420
ggcaaggcct tcaagttctt tcattggaac agcaatctga ctatcctgaa gaccaacatt     480
tctcacaatg aacctacca ttgcagcgga atggggaagc atcgctatac ttctgctggg     540
atcagtgtga ccgtcaaaga actgttccca gctcccgtgc tgaacgcatc cgtcacatct     600
cctctgctgg aggggaatct ggtgacactg tcctgtgaaa ctaagctgct gctgcagcgg     660
ccaggactgc agctgtactt ctccttttat atgggctcta aaaccctgag gaggcgcaac     720
acaagctccg agtaccagat tctgactgcc ggagggaag acagcgggct gtattggtgc     780
gaggccgcta ccgaagatgg taatgtgctg aagaggtccc ccgagctgga actgcaggtg     840
ctgtctagtg gcggaggggg tagtcaggtg cagctggtcc agtccggagg aggagtggtc     900
cagcctggca ggtcactgag actgagctgt aagtcaagcg atacaccttt acaagatat     960
actatgcact gggtgcgcca ggctcctggt aaaggactgg agtggatcgg gtacattaac    1020
cctagcagag gttacacaaa ctataatcag aaggtgaaag accgcttcac aatctcccga    1080
gataactcta aaaatactgc ctttctgcag atggactccc tgagacctga ggataccggc    1140
gtgtactttt gcgctcgcta ctatgacgat cattactgtc tggattattg gggacagggg    1200
acccccagtga cagtctcctc tgtggaaggt ggcagtggag ggtcaggtgg cagcggaggg    1260
tccggtggag tggacgatat ccagatgacc cagtctccca gttcactgtc tgccagtgtg    1320
ggcgaccggg tcactattac ctgcagggct agctcctctg tgagctacat gaattggtat    1380
cagcagaccc ctggcaaggc accaaaaacga tggatctacg ataccagtaa ggtggcctca    1440
ggagtcccaa gccggttctc aggtagcggc tccggaacag actataccct caccatcagt    1500
```

-continued

```
tcactgcagc ctgaggatat tgccacttac tattgtcagc agtggagtag taatcctctg    1560
acattcggac agggaaccaa actgcagatc acataa                              1596
```